US 8,795,978 B2

(12) United States Patent
Steyn et al.

(10) Patent No.: US 8,795,978 B2
(45) Date of Patent: Aug. 5, 2014

(54) **MODULATING LATENCY AND REACTIVATION OF *MYCOBACTERIUM TUBERCULOSIS***

(75) Inventors: Adrie J. C. Steyn, Hoover, AL (US); Ashwani Kumar, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 825 days.

(21) Appl. No.: 12/666,008

(22) PCT Filed: Jun. 20, 2008

(86) PCT No.: PCT/US2008/067714
§ 371 (c)(1),
(2), (4) Date: May 6, 2010

(87) PCT Pub. No.: WO2009/035742
PCT Pub. Date: Mar. 19, 2009

(65) Prior Publication Data
US 2010/0239691 A1 Sep. 23, 2010

Related U.S. Application Data

(60) Provisional application No. 60/945,707, filed on Jun. 22, 2007.

(51) Int. Cl.
*C12Q 1/48* (2006.01)
*C12Q 1/02* (2006.01)

(52) U.S. Cl.
USPC .............................. 435/15; 435/29; 435/253.1

(58) Field of Classification Search
None
See application file for complete search history.

(56) References Cited

U.S. PATENT DOCUMENTS 5,023,252 A    6/1991  Hseih
7,566,550 B2 * 7/2009  Tyagi et al. .................... 435/15

OTHER PUBLICATIONS

Sardiwal et al. "A GAF Domain in the Hypoxia/NO-inducible *Mycobacterium tuberculosis* DosS Protein Binds Haem". J. Mol. Biol. (2005) 353: 929-936.*
Berry and Trumpower, "Simultaneous determination of hemes a, b, and c from pyridine hemochrome spectra," Anal. Biochem. 161:1-15 (1987).
Botha et al., "Reactivation of latent tuberculosis by an inhibitor of inducible nitric oxide synthase in an aerosol murine model," Immunol. 107:350-7 (2002).
Chan et al., "Effects of nitric oxide synthase inhibitors on Murine infection with *Mycobacterium tuberculosis*," Infect. Immun. 63:736-40 (1995).
Delgado-Nixon et al., "Dos, a heme-binding PAS protein from *Escherichia coli*, is a direct oxygen sensor," Biochemistry 39:2685-91 (2000).

Gilles-Gonzalez and Gonzalez, "Heme-based sensors: defining characteristics, recent developments, and regulatory hypotheses," J. Inorg. Biochem., 99:1-22 (2005).
Gilles-Gonzalez et al., "Heme-based sensors, exemplified by the kinase FixL, are a new class of heme protein with distinctive ligand binding and autoxidation," Biochemistry 33:8067-73 (1994).
Ioanoviciu et al., "DevS, a heme-containing two-component oxygen sensor of *Mycobacterium tuberculosis*," Biochemistry 46:4250-60 (2007).
King, "Molecular and culture-based analyses of aerobic carbon monoxide oxidizer diversity," Appl. Environ. Microbiol. 69:7257-65 (2003).
King, "Uptake of carbon monoxide and hydrogen at environmentally relevant concentrations by mycobacteria," Appl. Environ. Microbiol. 69:7266-72 (2003).
Kumar et al., "*Mycobacterium tuberculosis* DosS is a redox sensor and DosT is a hypoxia sensor," Proc. Natl. Acad. Sci. USA 104:11568-73 (2007).
MacMicking et al., "Identification of nitric oxide synthase as a protective locus against tuberculosis," Proc. Natl. Acad. Sci. USA 94:5243-8 (1997).
Martin et al., "Ligand selectivity of soluble guanylyl cyclase: effect of the hydrogen-bonding tyrosine in the distal heme pocket on binding of oxygen, nitric oxide, and carbon monoxide," J. Biol. Chem. 281:27836-45 (2006).
Nathan and Shiloh, "Reactive oxygen and nitrogen intermediates in the relationship between mammalian hosts and microbial pathogens," Proc. Natl. Acad. Sci. USA 97:8841-8 (2000).
Ohno et al., "The effects of reactive nitrogen intermediates on gene expression in *Mycobacterium tuberculosis*," Cell Microbiol. 5:637-48 (2003).
Park et al., "Growth of mycobacteria on carbon monoxide and methanol," J. Bacteriology 185:142-7 (2003).
Roberts et al., "Two sensor kinases contribute to the hypoxic response of *Mycobacterium tuberculosis*," J. Biol. Chem. 279(22):23082-7 (2004).

(Continued)

*Primary Examiner* — Vera Afremova
(74) *Attorney, Agent, or Firm* — Kilpatrick Townsend & Stockton LLP

(57) ABSTRACT

Methods for screening for agents that modulate the activation state, i.e., active growth or persistence, of *Mycobacterium tuberculosis* (Mtb), methods of treating an Mtb infection in a subject using agents identified by the screening methods, and methods for screening for a latent Mtb infection in a subject are disclosed. The screening methods involve contacting a Mtb sensor kinase with an agent to be tested, then detecting the response of the Mtb sensor kinase to modulating ligands or detecting changes in the oxidation state of the heme iron of the Mtb sensor kinase. The methods for treating an Mtb infection in a subject involve administering a therapeutically effective amount of an agent identified by the screening methods. The methods for screening for a latent Mtb infection in a subject involve detecting carbon monoxide or nitric oxide binding to heme iron of Mtb sensor kinases.

17 Claims, 7 Drawing Sheets

(56) References Cited

OTHER PUBLICATIONS

Romberg and Kassner, "Nitric oxide and carbon monoxide equilibria of horse myoglobin and (N-methylimidazole) protoheme. Evidence for steric interaction with the distal residues," Biochemistry 18:5387-92 (1979).

Saini et al., "DevR-DevS is a bona fide two-component system of *Mycobacterium tuberculosis* that is hypoxia-responsive in the absence of the DNA-binding domain," Microbiol. 150:865-75 (2004).

Springer et al., "Discrimination between oxygen and carbon monoxide and inhibition of autooxidation by myoglobin," J. Biol. Chem. 264:3057-60 (1989).

\* cited by examiner

MODULATING LATENCY AND REACTIVATION OF *MYCOBACTERIUM TUBERCULOSIS*

STATEMENT REGARDING FEDERALLY SPONSORED RESEARCH

This invention was made with government support from the National Institutes of Health (Grant No. R01 AI058131). The United States government has certain rights in this invention.

BACKGROUND

*Mycobacterium tuberculosis* (Mtb) is responsible for over 2 million deaths annually. The success of Mtb as a pathogen is related, at least in part, to its ability to persist, i.e., remain in an inactive or latent state, for years or decades in humans without manifesting any clinical symptoms. In fact, experts have estimated that approximately two billion people, roughly one third of the world's population, are latently infected with Mtb.

SUMMARY

Methods for screening for agents that modulate the activation state, i.e., active growth or persistence, of Mtb are disclosed. These methods involve contacting an Mtb sensor kinase with an agent to be tested, then detecting the response of the Mtb sensor kinase to the presence of ligands such as oxygen, carbon monoxide, or nitric oxide as well as changes in the oxidation state of the heme iron of the Mtb sensor kinase. Also disclosed are methods for modulating the activation state of Mtb in a subject by administering an agent identified by the screening methods disclosed. Further disclosed are methods of modulating latency of Mtb in a subject with an Mtb infection by administering an effective, non-lethal dose of carbon monoxide.

Methods of screening for Mtb in a subject by detecting carbon monoxide or nitric oxide binding to heme iron of Mtb sensor kinases in a sample from a subject are also disclosed. In these methods, the presence of Mtb sensor kinase heme iron bound carbon monoxide or nitric oxide indicates that Mtb is in the subject.

BRIEF DESCRIPTION OF THE DRAWINGS

FIG. 4A shows a UV-visible characterization of DosS (3 µM in 20 mM Tris, pH 7.5) as purified, exposed to dithionite (DTH) or treated with DTH and re-exposed to air. The inset is an enlarged image of the 500-600 nm region. FIG. 4B shows a continuous wave (cw) X-band electron paramagnetic resonance (EPR) spectroscopy analysis of air exposed DosS (6 µM in 20 mM Tris, pH 7.5). FIG. 4C shows a UV-visible spectrum of DosS as purified, exposed to air after DTH treatment, the former treated with KCN or $Fe(CN)_6^{3-}$. Note the characteristic met-CN peak at 540 nm. Numbers in parentheses indicate absorption maximum in nm.

FIG. 5A shows a UV-visible spectroscopy characterization of DosT (3 µM in 20 mM Tris, pH 7.5) as purified, exposed to DTH, followed by air exposure. The inset is an enlarged image of the 500-600 nm region. FIG. 5B shows a cw X-band EPR spectroscopy analysis of as purified DosT (6 µM in 20 mM Tris, pH 7.5) after treatment with $Fe(CN)_6^{3-}$. No EPR signal was detected with purified DosT without $Fe(CN)_6^{3-}$ exposure. FIG. 5C shows a UV-visible spectrum of DosT exposed to air followed by DTH treatment, the former treated with potassium cyanide (KCN), and exposed to $Fe(CN)_6^{3-}$ followed by KCN. Numbers in parentheses indicate absorption maximum in nm.

FIG. 6A shows a UV-visible spectroscopy characterization of DosS exposed to DTH, and exposed to NO, or CO. FIG. 6B shows an EPR spectroscopy analysis of DosS (6 µM) treated with DTH followed by NO. FIG. 6C shows UV-visible spectroscopy results for DosT exposed to DTH, and exposed to NO or CO. FIG. 6D shows EPR spectroscopy analysis of DosT (6 µM) treated with DTH followed by NO. FIG. 6E shows UV-visible spectroscopy results for oxy-DosT exposed to NO or CO. Numbers in parentheses indicate absorption maximum in nm.

FIG. 7A shows the effect of NO on the autokinase activity of DosS ($Fe^{3+}$) and DTH reduced DosS ($Fe^{2+}$). FIG. 7B shows the autokinase activity of DosS that was exposed to DTH to generate that $Fe^{2+}$ form followed by treatment with $Fe(CN)_6^{3-}$ to generate met DosS ($Fe^{3+}$) is shown. FIG. 7C shows the effect of CO on the autokinase activity of DosS ($Fe^{3+}$) and DTH reduced DosS ($Fe^{2+}$). Numbers indicate minutes of incubation.

FIG. 8A shows the effect of NO on the autokinase activity of deoxy DosT ($Fe^{2+}$) and oxy DosT ($Fe^{2+}$—$O_2$). FIG. 8B shows the effect of CO on the autokinase activity of deoxy DosT ($Fe^{2+}$) and oxy DosT ($Fe^{2+}$—$O_2$). Numbers indicate minutes of incubation.

DETAILED DESCRIPTION

Figure 1:
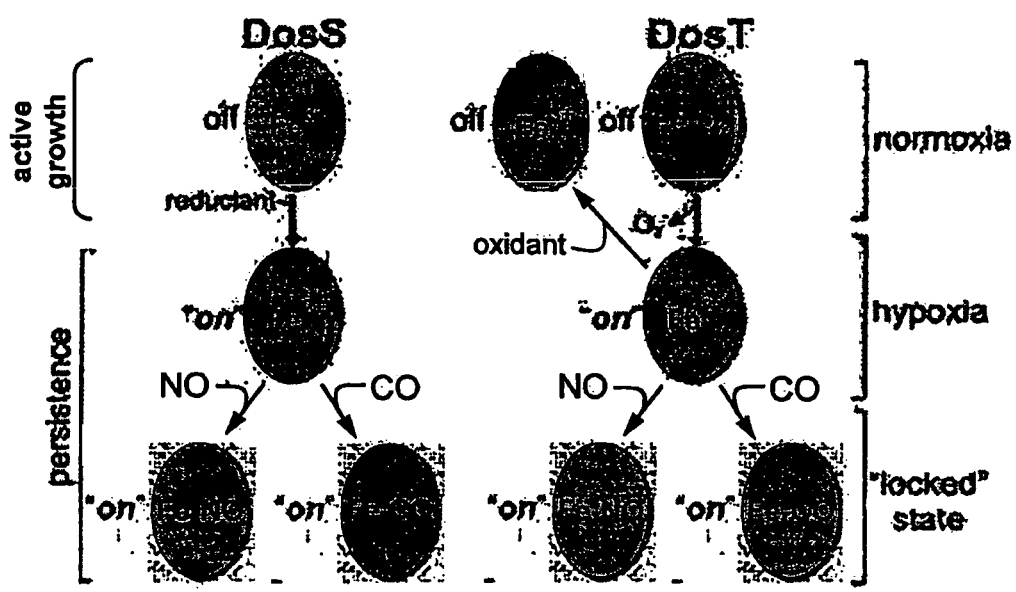
FIG. 1 shows a model for the role of Mtb DosS and DosT in the shift-down of tubercle bacilli to the persistent state.

*Mycobacterium tuberculosis* (Mtb) sensor kinases DosS (Rv3132c) and DosT (Rv2027c) were determined to contain a heme prosthetic group. Furthermore, the oxidation/reduction (charge) state of the heme-iron and the presence of bound ligands oxygen ($O_2$), nitric oxide (NO), or carbon monoxide (CO) on the heme iron was determined to be indicative of whether Mtb is in an active growth or persistent (latent) state. FIG. 1 shows a model indicating the role of the Mtb sensor kinases DosS and DosT in the shift-down of Mtb tubercle bacilli to the persistent state.

As shown in FIG. 1, when DosS is exposed to normal levels of oxygen, i.e., normoxia, its heme iron is in the $Fe^{3+}$ charge state and in DosT the heme iron has bound $O_2$ (oxy DosT). FIG. 1 also indicates that DosS shifts to the persistent, i.e., latent, state with the aid of a reductant and DosT shifts to persistent state through the loss of $O_2$ under hypoxic conditions to generate ferrous ($Fe^{2+}$) DosT. FIG. 1 further shows how both DosS and DosT can be "locked" in the persistent state by binding either CO or NO. FIG. 1 additionally indicates that the heme iron ($Fe^{2+}$) of a deoxygenated DosT can be oxidized to a $Fe^{3+}$ charge state, which results in Mtb tubercle bacilli's return to an active growth state (i.e., reactivation of the Mtb).

Agents that control or modulate the oxidation or ligation state of Mtb sensor kinases, such as DosS and DosT, are used to selectively control the persistence or active growth state of Mtb. Such control of Mtb is exploited in the treatment of Mtb positive subjects. For example, agents that control or modulate the oxidation or ligation state of Mtb sensor kinases are used to force latent Mtb to enter the active growth state under optimal treatment conditions or drive Mtb in an active growth state into a persistent state until optimal treatment conditions are met.

Methods of screening for agents that modulate the activation state of, reactivate, or prevent latency in Mtb are disclosed herein. Methods that promote, induce, modulate, and reduce Mtb latency also are disclosed herein. Further, methods of screening for Mtb in a subject are disclosed herein.

A method of screening for an agent that modulates the activation state of Mtb involves contacting an Mtb sensor kinase with the agent to be tested, and detecting binding of oxygen, nitric oxide, carbon monoxide, or any combination thereof to one or more sensor kinases (e.g., to a first and second sensor kinase) in the presence of the agent. In this method, a change in binding as compared to a control level of binding indicates that the agent modulates the activation state of Mtb. The Mtb sensor kinase can be DosS, DosT, or a mixture of DosS and DosT. The change in binding is detected by monitoring the binding or absence of binding of $O_2$, NO, or CO from either the Mtb sensor kinase in general or monitoring the heme prosthetic group specifically for the level of binding. By detecting binding therefore is meant to include the absence of binding as well as the presence of binding. Further, binding can be detected by detecting a change in a heme prosthetic group of a sensor kinase. A change in a heme prosthetic group can include changes such as a change due to the binding or loss of a ligand, a change in the oxidation state of the heme iron, or a change in the conformation of the heme group. Optionally, the binding level is quantified. As used herein, a control level of binding refers to the level of binding of a similar sample that has not been exposed to the agent to be tested, but otherwise is treated the same as the sample treated with the agent.

When an agent reduces the binding of NO or CO to an Mtb sensor kinase, that agent promotes the reactivation of Mtb. The loss or reduction of bound NO or CO is indicative of promoting the reactivation of Mtb because the Mtb sensor kinase is no longer in the locked state and can be converted to the normoxic state. Similarly, when an agent promotes the binding of $O_2$ to a Mtb sensor kinase such as DosT, the agent is promoting the reactivation of Mtb. Further, when an agent increases the binding of NO or CO or reduces the binding of $O_2$ in Mtb sensor kinases, that agent promotes persistence in Mtb.

When screening an agent for its effect on NO or CO binding, the Mtb sensor kinase can be placed into the persistent state prior to contacting the sensor kinase to NO or CO. For example, in the case of DosT, the sensor kinase can be deoxygenated and in the case of DosS, the oxidation state of the sensor kinase can be reduced (via a reductant) prior to the contacting step.

Agents identified by the screening methods disclosed herein can be administered to a subject to modulate the activation state of Mtb. Because treatments for a latent Mtb infection are not yet known, the ability to cause Mtb to enter into the active growth state under controlled conditions under which Mtb can be treated can be beneficial. For example, to treat Mtb in a subject with no clinical symptoms, i.e., a subject with a latent Mtb infection, the Mtb can first be changed to the active growth state in order to be treated. Analogously, for example, in a subject exhibiting clinical symptoms of an Mtb infection, the ability to cause Mtb to enter the persistent state until optimum treatment conditions are met can be beneficial.

Latency of Mtb is promoted in a subject, such as a mammal, by administering to the subject an effective, non-lethal dose of CO. If Mtb is in the active growth state, the CO causes hypoxia and induces persistence, i.e., latency. CO binds to the heme iron of a Mtb sensor kinase, such as DosT or DosS to lock the sensor kinase in the persistent state. The oxidation or oxygenation state of the heme iron of Mtb sensor kinases in a sample from the subject can be determined after a dose of CO to determine if an additional non-lethal dose of CO is necessary to further promote latency. For example, the oxygenation state of the heme iron of DosT can be determined in a sample from the subject and, if any DosT with oxygen bound to the heme iron remains, an additional dose of CO can be given to further promote latency. Similarly, for example, the oxidation state of DosS can be determined, and if heme iron in the $Fe^{3+}$ charge state is still present, an additional dose of CO can be given to promote latency. An effective, non-lethal dose of CO can be delivered, for example, by inhalation. An example of an effective, non-lethal inhalation dose of CO is between about 250 ppm and about 1000 ppm.

In addition to promoting latency by delivering CO to a subject, latency can also be reduced by reducing the level of CO in blood plasma. Blood plasma CO levels can be reduced, for example, by dialyzing blood against a dialysate system that removes CO.

Provided herein is a method for screening for an agent that modulates the activation state of *Mycobacterium tuberculosis* (Mtb) that involves the steps of contacting an Mtb sensor kinase with the agent to be tested and detecting a change in oxidation state of a heme iron in the Mtb sensor kinase. A change in oxidation state as compared to a control indicates the agent modulates the activation state of Mtb. As shown in FIG. 1, the heme iron of DosS undergoes a change in oxidation state when Mtb undergoes a change in activation state, i.e., active growth to persistent or vice versa. Thus, an increase in the oxidation state of the heme iron of DosS from $Fe^{2+}$ to $Fe^{3+}$ indicates a change from the persistent state to the active growth state, and conversely, a change from $Fe^{3+}$ to $Fe^{2+}$ indicates a change from the active growth state to the persistent state. Additionally, the heme iron of DosT in a persistent state, i.e., in the $Fe^{2+}$ oxidation state, can be oxidized to the $Fe^{3+}$ charge state if an oxidizing agent is present. If the Mtb sensor kinase used in the method is placed in the persistent state prior to the contacting step, the method will indicate if the agent promotes a change to the active growth state. Similarly, if the Mtb sensor is placed in the active growth state prior to the contacting step, the method will indicate if the agent promotes a change to the latent state.

Also provided is a method for screening for an agent that reactivates latent Mtb involving the steps of contacting one or more Mtb sensor kinases with NO or CO, contacting the Mtb sensor kinase with the agent to be tested, and detecting the oxidation and/or oxygenation state of a heme iron of the Mtb sensor kinase. An increase in oxidation or oxygenation as compared to a control indicates the agent reactivates Mtb. The Mtb sensor kinase can be DosS, DosT, or a mixture of DosS and DosT. Detection of both oxidation and oxygenation (or ligation) can be performed. Performing detection of both oxidation and oxygenation (or ligation) can be useful when a mixture of sensor kinases are present, such as, for example, a mixture of DosS and DosT.

Further provided is a method for screening for an agent that prevents latency in Mtb involving the steps of providing a Mtb sensor kinase DosS, wherein the DosS contains a $Fe^{3+}$ heme iron, contacting the Mtb sensor kinase with the agent to be tested, contacting the Mtb sensor kinase with CO or NO, and detecting the $Fe^{3+}$ heme iron. $Fe^{3+}$ heme iron indicates that the agent prevents latency. As shown in FIG. 1, when the DosS heme iron is in the $Fe^{3+}$ oxidation state, Mtb is in the active growth state. Thus, after contact with an agent and exposure to CO or NO, if the DosS heme iron oxidation state remains at $Fe^{3+}$, the agent prevents latency.

Also provided is a method for screening for an agent that prevents latency in Mtb involving the steps of providing a Mtb sensor kinase DosT, wherein the DosT comprises a heme iron-$O_2$ complex, contacting the Mtb sensor kinase with the agent to be tested, contacting the Mtb sensor kinase with CO or NO, and detecting the heme iron-oxygen complex. Heme iron-oxygen complex indicates that the agent prevents latency. As shown in FIG. 1, when a DosT heme iron has bound $O_2$, active growth is indicated. Thus, after contact with an agent and exposure to CO or NO, if the DosT heme-oxygen complex is still detected, the agent prevents latency.

Latency of Mtb can be induced in a subject with an Mtb infection by inducing activation of heme oxygenase I (HO-I). Heme oxygenase (HO) is an enzyme that catalyzes the degradation of heme producing the degradation products iron, carbon monoxide and biliverdin. HO cleaves the heme ring at the alpha methene bridge to form biliverdin (verdoglobin if still attached to globin). Heme oxygenase I (HO-I) is an inducible enzyme isoform of heme oxygenase that responds to environmental stresses such as oxidative stress, hypoxia, heavy metals, and cytokines. Because carbon monoxide is produced when HO-I degrades heme, providing heme (or the precursor hemin) to a subject produces carbon monoxide and additional carbon monoxide induces latency as discussed above. Thus, latency of Mtb is induced in a subject with an Mtb infection by activating an HO, such as HO-I. HO can be activated by administering to the subject a therapeutically effective amount of heme (which will induce the HO to degrade heme and produce carbon dioxide). Thus, latency of Mtb is induced in a subject with an Mtb infection by administering to the subject a therapeutically effective amount of heme or hemin. As an example, HO-I can be induced by administration of a therapeutically effective amount of hemin (i.e., heme chloride), such as between about 10 mg/kg/day and about 20 mg/kg/day, i.e., about 15 mg/kg/day. As a further example, HO-I can be induced by molecules other than heme such as, for example, Co-protoporphyrin. Thus, to induce HO-I, Co-protoporphyrin can be administered at about 40 μmol/kg body weight to about 50 μmol/kg body weight, i.e., about 50 μmol/kg body weight.

Latency of Mtb can be maintained in a subject with an Mtb infection by inducing activation of inducible nitric oxide synthase (iNOS). iNOS is an enzyme that generates NO in response to certain cytokines, such as interferon-gamma (γ-IFN), tumor necrosis factor (TNF), interleukin-1 and -2 (IL-1 and IL-2), and lipopolysaccharides (LPS). After cytokine induction, iNOS exhibits a delayed activity response which is then followed by a significant increase in NO production over a long period of time. NO produced by iNOS is important for early immune responses to invading organisms. Because NO is produced by iNOS, inducing activation of iNOS produces NO and additional NO in a subject with an Mtb infection maintains latency as discussed above. Thus, latency of Mtb can be maintained in a subject with an Mtb infection by inducing activation of iNOS. iNOS can be activated by administering a therapeutically effective amount of a cytokine such as, for example, γ-IFN, TNF, TNF-α, IL-1, IL-1β, IL-2, LPS, NF-kappa beta, signal transducer and activator of transcription-1α (STAT-1α). As an example, a therapeutically effective amount of γ-IFN can be between about 15 ng/mL and about 25 ng/mL, i.e., about 20 ng/mL.

Additionally, a subject that is not exhibiting clinical symptoms of Mtb can be screened for persistent Mtb by detecting CO or NO binding to Mtb sensor kinases in a sample from the subject. The presence of Mtb sensor kinases with bound CO or NO in the sample from the subject indicates that the subject has a persistent Mtb infection. The Mtb sensor kinase can be, for example, DosS or DosT. As shown in FIG. 1, when the heme iron of DosS or DosT binds NO or CO the Mtb are locked in the persistent, i.e., latent, state. Therefore, the presence of Mtb sensor kinases with NO or CO bound to their heme iron indicates the presence of Mtb in the latent state. Similarly, the presence of $Fe^{2+}$ DosS or $Fe^{2+}$ DosT would also indicate Mtb in the persistent state. Conversely, the presence of oxy DosT or $Fe^{3+}$ DosS would indicate the presence of Mtb in the active growth state.

The binding (or absence of binding) of $O_2$, NO, and CO to an Mtb sensor kinase can be detected by electronic absorption spectroscopy. For example, UV-visible absorption spectra can be used to detect $O_2$, NO, or CO bound to a heme iron or to detect the absence of binding. Specifically, changes in the UV-visible spectrum can indicate changes in binding at the heme iron. The UV-visible spectral changes for heme iron binding to $O_2$, NO, and CO are well characterized and well known to those of skill in the art. As used herein, the detection of binding is intended to encompass detecting the presence or absence of binding as well as the level of binding. Exemplary methods are provided in the Examples.

The charge state of the heme iron of the Mtb sensor kinases discussed herein can be determined, for example, by electron paramagnetic resonance (EPR) spectroscopy as well as atomic absorption spectroscopy. EPR is a technique useful in studying chemical species that have one or more unpaired electrons, such as heme iron. The EPR spectral characteristics of various heme iron oxidation states as well as the spectral characteristics indicating the binding to ligands such as $O_2$, CO, and NO to heme iron are well characterized and well known to those of skill in the art. Additionally, the charge state of the heme iron can be determined by electronic absorption spectroscopy as well characterized and well known to those of skill in the art. Examples of characterization and detection by EPR are provided in the Examples.

Additional chemical methods are available for determining the charge state of a heme iron of an Mtb sensor kinase. For example, $Fe^{3+}$ heme iron reacts with potassium cyanide (KCN) to produce a heme-CN complex, which produces a peak at 540 nm in the atomic absorption spectrum. Thus, the presence of $Fe^{3+}$ heme iron can be detected in this manner. Further, $Fe^{2+}$ heme iron is oxidized by $Fe(CN)_6^{3-}$ to generate heme iron in a $Fe^{3+}$ oxidation state that can then be reacted with KCN to produce the characteristic atomic absorption peak at 540 nm. Methods such as these for determining the charge state of a heme iron are well known to those of skill in the art and examples of their use are included in the examples below.

Samples useful for the screening methods above include bodily fluids that are likely to include Mtb tubercle bacilli, such as, blood, mucus, phlegm, sputum, pus, lung biopsy, etc.

Further provided are kits for performing the screening methods disclosed herein. Such kits can include one or more Mtb sensor kinases optionally attached to a solid support or further comprising a means for attaching to a solid support. The kits can include any one or more of $O_2$, CO, NO, oxidants, and reductants. Kits as described herein can contain any combination of Mtb sensor kinases (e.g., DosS, DosT, or combinations of DosS and DosT); any combination of $O_2$, CO, NO, oxidants, and reductants; or any combinations of both.

When agents disclosed herein or determined by a screening method disclosed herein are provided to a subject, the agents can be provided in a pharmaceutically acceptable form or composition. By "pharmaceutically acceptable" is meant a material that is not biologically or otherwise undesirable, and which can be administered to an individual along with the selected substrate without causing significant undesirable biological effects or interacting in a deleterious manner with any of the other components of the pharmaceutical composition in which it is contained.

Further provided is a method of making an agent that modulates the activation state of Mtb involving identifying an agent using one of the screening methods disclosed herein and making a pharmaceutically acceptable dosage form for providing to a patient that includes the dosage form. Dosage forms created by this method can also be packaged in individual or multiple dosage forms. Such packaging can maintain the viability and efficacy of the dosage form.

Pharmaceutical compositions containing agents disclosed herein or identified using methods disclosed herein can be prepared by mixing the desired agents with an appropriate vehicle suitable for the intended route of administration, optionally for use in an appropriate drug delivery device. In making pharmaceutical compositions, the agents can be mixed with an excipient, diluted by an excipient or enclosed within such a carrier which can be in the form of a capsule, paper or other container. When the pharmaceutically acceptable excipient serves as a diluent, it can be a solid, semi-solid, or liquid material, which acts as a vehicle, carrier or medium for the therapeutic agent. Thus, the compositions can be in the form of tablets, pills, powders, lozenges, elixirs, suspensions, emulsions, solutions, syrups, aerosols (as a solid or in a liquid medium), ointments containing, for example, up to 10% by weight of the therapeutic agents, soft and hard gelatin capsules, suppositories, sterile injectable solutions, and sterile packaged powders.

Some examples of suitable excipients include artificial biological fluid, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include lubricating agents such as talc, magnesium stearate, and mineral oil; wetting agents; emulsifying and suspending agents; preserving agents such as methyl- and propylhydroxy-benzoates; sweetening agents; and flavoring agents. The agents disclosed herein or identified using methods disclosed herein can be formulated so as to provide quick, sustained or delayed release of the agents after administration to the subject by employing procedures known in the art.

For preparing solid compositions such as tablets, an agent is mixed with a pharmaceutical excipient to form a solid preformulation composition containing a homogeneous mixture of the agent. When referring to these preformulation compositions as homogeneous, it is meant that the agents are dispersed evenly throughout the composition so that the composition may be readily subdivided into equally effective unit dosage forms such as tablets, pills and capsules. These tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the agents disclosed herein or identified using methods disclosed herein may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. The compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine.

Solution, suspension, or powder compositions may be administered, preferably orally or nasally, from drug delivery devices which deliver the formulation in an appropriate manner. Another formulation employed in the methods described herein employs transdermal delivery devices ("patches"). Such transdermal patches may be used to provide continuous or discontinuous infusion of the therapeutic agents in controlled amounts. The construction and use of transdermal patches for the delivery of pharmaceutical agents is well known in the art. See, for example, U.S. Pat. No. 5,023,252, herein incorporated by reference. Such patches may be constructed for continuous, pulsatile, or on demand delivery of pharmaceutical agents. Other suitable formulations for use with the agents described herein can be found in Remington's Science and Practice of Pharmacy, 21st Edition, ed. University of the Sciences in Philadelphia, Lippincott, Williams & Wilkins, Philadelphia Pa., 2005.

An effective amount is an amount of an agent disclosed herein or identified using methods disclosed herein sufficient to achieve the intended purpose. Similarly, an effective, non-lethal dose of carbon monoxide is an amount sufficient to achieve the intended purpose without causing death. For example, an effective amount of an agent disclosed herein or identified using methods disclosed herein that reduces or prevents latency of Mtb, is an amount sufficient, in vivo or in vitro, as the case may be, to reduce or prevent at least a portion, and preferably all, of Mtb tubercle bacilli from staying in or entering the latent state. Similarly, an effective amount of an agent disclosed herein or identified using methods disclosed herein that reduces or prevents active growth of Mtb, is an amount sufficient, in vivo or in vitro, as the case may be, to prevent at least a portion, and preferably all, of Mtb tubercle bacilli from entering the active growth state. An effective, non-lethal dose is an amount, in vivo or in vitro, as the case may be, to prevent at least a portion, and preferably all, of Mtb tubercle bacilli from entering the active growth state. The effective amount of a given agent and an effective, non-lethal dose will vary with factors such as the nature of the agent, the route of administration, the size and species of the subject to receiving the therapeutic agent, and the purpose of the administration. The effective amount or effective, non-lethal dose in each individual case may be determined empirically by a skilled artisan according to established methods in the art.

As used herein, a drug delivery device is an object suitable for administration of an effective amount of an agent disclosed herein or identified using methods disclosed herein. A drug delivery device can effect administration of an agent disclosed herein or identified using methods disclosed herein by any method established in the art, including, for example, parenteral, intravenous, intra-arterial, intracolonic, intratracheal, intraperitoneal, intranasal, intravascular, intrathecal, intracranial, intramarrow, intrapleural, intradermal, transdermal, subcutaneous, intramuscular, intraperitoneal, oral, rectal, vaginal, topical administration, pulmonary administration, or any combination thereof. Systemic delivery can be accomplished by techniques including, for example, parenteral, intravenous, intra-arterial, intracolonic, intratracheal, intraperitoneal, intranasal, intravascular, intrathecal, intracranial, intramarrow, intrapleural, intradermal, transdermal, subcutaneous, intramuscular, intraperitoneal, oral, rectal, vaginal, topical administration, pulmonary administration, or any combination thereof. A drug delivery device can be, for example, an implantable device or a pump (e.g., an osmotic pump), depot (slow release) delivery of formulation, or an injector pen (with or without a needle). Optionally, the drug delivery device is an infusion device or component thereof or, alternatively, is a device for other means than infusion.

As used herein, treating means treating or ameliorating, and treating or ameliorating means the reduction or complete removal of one or more symptoms of a disease or medical condition, such as tuberculosis. Such treatment or amelioration can include the delay or elimination of the onset of one or more symptoms when administered to a person at risk for the disease or medical condition. Tests for the success of treatment or amelioration are well known in the art.

A subject treated using an agent disclosed herein or identified using methods disclosed herein can be of any age, including a child, juvenile or an adult.

The examples below are intended to further illustrate certain embodiments of the invention, and are not intended to limit the scope of the claims.

EXAMPLES

For Examples 1 to 4, the following materials and methods were used:

Cloning, Expression and Purification of DosS and DosT.

The complete open reading frames of dosS and dosT were PCR-amplified from Mtb H37Rv genomic DNA and cloned into pET15b (Novagen Darmstadt, Germany). To generate His-SUMO-tagged gene products, dosS and dosT PCR products were cloned in-frame with the 11 kDa small ubiquitin related modifier (SUMO) tag in pET15b. SUMO is a small eukaryotic polypeptide that increases solubility of bacterial proteins. His-tagged or His-SUMO-tagged fusion proteins were overproduced in *E. coli* Rosetta (DE3) cells in Luria Broth (Difco; Franklin Lakes, N.J.) supplemented with 20 pM hemin. Purified DosS and DosT were obtained in both the soluble and insoluble fractions. Soluble proteins were extracted using Profinity™ IMAC Ni-charged resin (Biorad; Hercules, Calif.) as recommended by the manufacturer. His-tag and His-SUMO-tagged proteins gave identical absorption, EPR spectroscopy, and autokinase results. Fresh DosS and DosT were prepared every two weeks.

Electronic Absorption Spectroscopy.

The absorption spectra of purified DosS or DosT (3 µM each) were analyzed at 23° C. in stoppered quartz cuvettes with a Beckman Coulter DU800 spectrophotometer unless specified otherwise. When necessary, protein samples were transferred to an anaerobic glove box (Plas Labs; Lansing, Mich.) and treated with 30 µM DTH before sealing the cuvettes and recording the spectra. For air exposed samples, aliquots of protein were exposed to air by pipetting for 30 seconds into the cuvettes. In all experiments, DTH was removed using D-Salt Polyacrylamide Desalting Columns (6K; Pierce; Rockford, Ill.).

To determine the oxidation status of the heme iron, air exposed protein was divided into two aliquots and treated with 300 µM KCN. The met form of heme reacts with KCN to produce a met-CN complex characterized by single peak at 540 nm. When necessary, samples were treated with 300 µM $Fe(CN)_6^{3-}$. Heme content was determined using previously described protocols (Berry, E. A. & Trumpower, B. L., *Anal. Biochem.*, 161:1-15, 1987).

To test whether CO and NO can act as ligands for DosS or DosT, samples were deoxygenated for 15 minutes with a constant flow of argon gas and transferred to the anaerobic glove box. Samples were then treated with DTH, and the DTH subsequently removed via size-exclusion chromatography. For NO exposure, protein samples were treated with a 200-fold molar excess proline NONOate (Cayman; Ann Arbor, Mich.). For CO exposure, a constant stream of CO (100%) was flushed through the protein samples.

EPR Spectroscopy.

Protein samples were transferred to Wilmad SQ EPR tubes (Wilmad Glass; Buena, N.J.) immediately before freezing the tubes in liquid nitrogen. EPR spectra were recorded with a Broker Elexsys/Oxford Cryostat EPR instrument with setting of 5.6 G modulation amplitude, 0.2 mW, 9.63 GHz microwave frequency, and 10 K of helium temperature. When necessary, EPR tubes were sealed inside the anaerobic glove box. Xband EPR spectroscopy was performed at a temperature of 8K, with a microwave frequency at 9.63 GHz and microwave power of 1 mW. Hemoglobin exposed to proline NONOate was used as a control in the spectroscopy analysis.

In-vitro Phosphorylation Assay.

In-vitro phosphorylation assays were performed according to previously described methods (Roberts et al., *J. Biol. Chem.*, 2004, 279:22) and analyzed on 4-20% Tris-HCl gradient PAGE gels, dried and exposed to X-ray film overnight at −80° C. Formation of a heme-nitrosyl/carbonyl complex was first confirmed by absorption spectroscopy before analyzing samples for autokinase activity. As an additional control, air exposed samples were also treated with proline NONOate. The effect of CO on autokinase activity was measured similarly as described for NO, except that protein samples were flushed with 100% CO for 30 seconds. All autokinase reactions were performed inside the glove box.

Example 1

Mtb DosS and Dos T are Heme Proteins

To investigate the mechanism of signal sensing and relay of the Mtb Dos regulon, biochemical characterization of DosS and DosT was initiated. Purified preparations of both DosS and DosT were found to yield a red color, showing the presence of heme. Most heme sensor proteins contain PAS domains that are frequently reported to function as input modules for sensing oxygen, redox potential and light; however, DosS (Rv3132c) and DosT (Rv2027c) lack a PAS domain. Rather, motif annotation has established that both DosS and DosT are GAF-domain (cGMP regulated phosphodiesterases, adenylyl cyclases, and FhlA) proteins. GAF-domain proteins are frequently involved in cyclic nucleotide binding and the sensing of small molecules.

Figure 2:
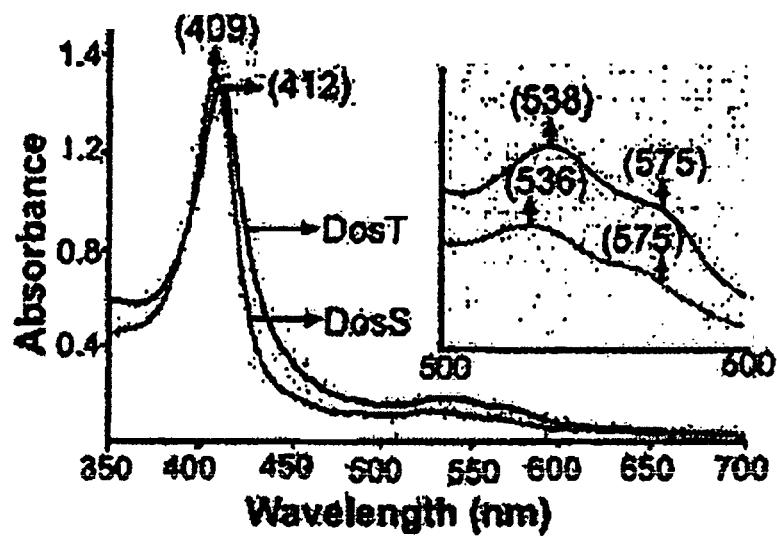
FIG. 2 shows the UV-visible spectra for purified DosS and DosT ($\alpha$, $\beta$ and Soret bands indicating the presence of a heme).
Figure 3:
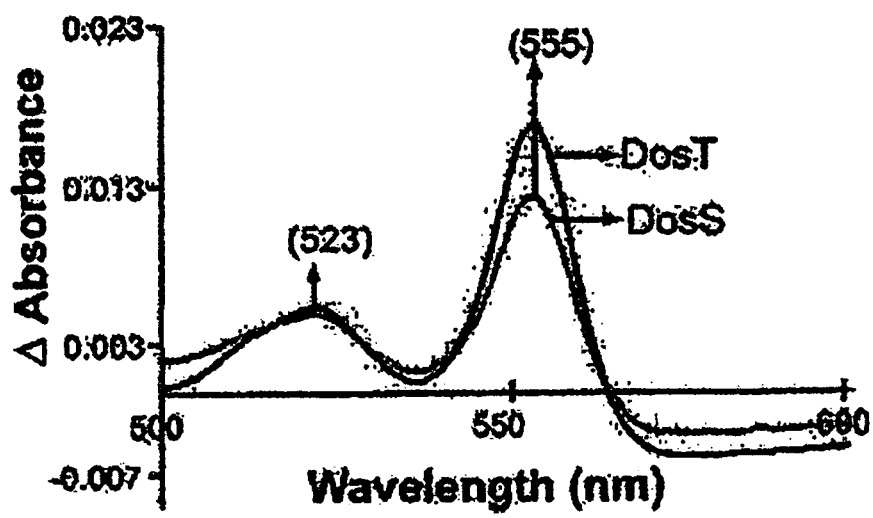
FIG. 3 shows the UV-visible spectra of DosS and DosT after pyridine haemochrome assay (spectra characteristic of heme type b).

UV-visible spectroscopy and the pyridine haemochrome assay (Berry, E. A. and Trumpower, B. L., Anal. Chem., 161:1-15 (1987)) were used to conclusively establish that both DosS and DosT are heme proteins, and to determine the type and spin state of the heme. As shown in FIG. 2, the UV-Vis spectra for DosS exhibits a sharp Soret (409 nm), α (575 nm), and β (536 nm) bands, in addition to another weak band at ~640 nm. These absorbances were indicative of a hexacoordinated, high-spin heme protein. As also shown in FIG. 2, the UV-Vis spectra for DosT exhibits Soret (412 nm), α (575 nm), and β (538 nm) bands. These absorbances were indicative of a hexa-coordinated heme protein. The pyridine haemochrome assay, as shown in FIG. 3, demonstrated that both native proteins bind approximately equimolar amounts of heme b. These results demonstrate that the GAF-containing proteins DosS and DosT bind heme as a prosthetic group.

DosS is in the met ($Fe^{3+}$) Form.

Heme-based sensor proteins are key regulators of adaptive responses to ligands such as $O_2$ and NO and are generally comprised of a heme-containing sensory domain that modulates the histidine kinase domain of the same protein. Bacterial heme sensor kinases are known to typically bind $O_2$ and are in the oxy form (Gilles-Gonzalez, M. A. & Gonzalez, O. J. Inorg. Biochem., 99: 1-22, 2005). In order to dissect the mechanism of the heme-iron mediated ligand sensing of DosS, EPR and UV-visible spectroscopy was used to examine the redox state of the heme-iron and whether $O_2$ is a ligand of DosS. First, the absorption spectra of aerobically purified DosS was compared with that of dithionite (DTH) exposed DosS. DTH exposure caused a shift in the Soret band (409 to 430 nm), and the α and β bands converged into a new peak at 557 nm (FIG. 4A), which resembles the deoxy form of FixL and hemoglobin (Gilles-Gonzalez et al., Biochemistry, 33:8067-73, 1994). Importantly, when this DTH exposed, i.e., reduced, sample was exposed to atmospheric oxygen, the absorption spectrum rapidly reverted back within seconds to that of native DosS (FIG. 4A).

Figure 4:
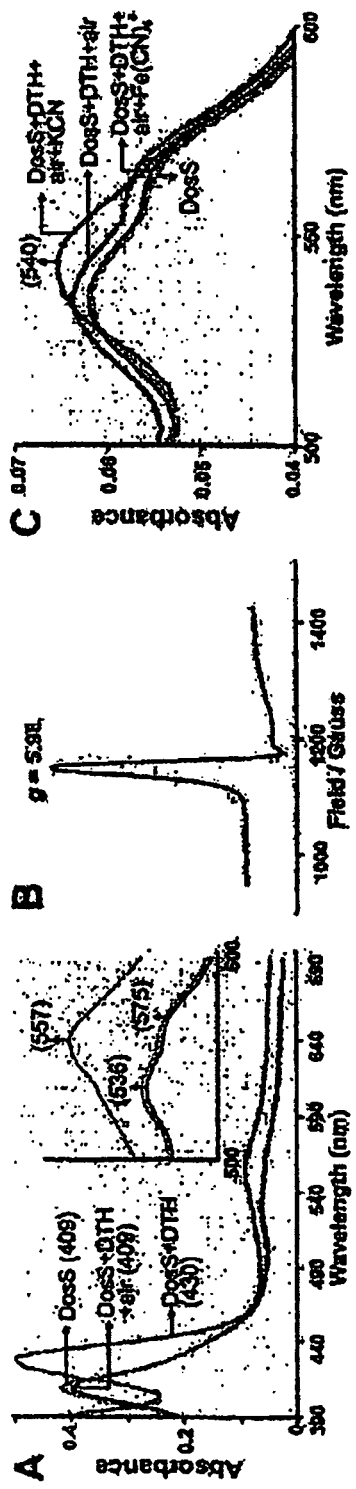
FIGS. 4 (A-C) show EPR and UV-visible spectroscopy characterization of DosS.

In order to conclusively determine the heme-iron oxidation status, EPR spectroscopy was used to demonstrate that $O_2$-exposed DosS gave a strong derivative signal centered at g=5.98, which is indicative of an axial, $Fe^{3+}$ high-spin species (FIG. 4B). These data indicate conclusively that, upon air exposure, reduced DosS is rapidly oxidized by $O_2$ to generate met DosS.

As an additional verification that the DosS heme-iron is oxidized rather than $O_2$-bound, the oxidation status of the DosS heme-iron post air exposure was determined by other independent techniques. Since the met ($Fe^{3+}$) form of heme reacts with KCN to produce a met-CN complex characterized by single peak at 540 nm, the spectral properties of KCN complexed with met heme proteins are routinely used to determine the oxidation status of heme iron. Reduced DosS was exposed to atmospheric oxygen for 30-120 seconds and then exposed to an excess of KCN. This caused the convergence of α and β bands into a single peak at 540 nm, which is indicative of a complex between met DosS and KCN, a finding which substantiates that the DosS heme iron is in the met form (FIG. 4C). Finally, air exposed DosS was treated with an excess of the oxidant $Fe(CN)_6^{3-}$ and no change was observed in the spectral properties of DosS (FIG. 4C). Taken together, these data demonstrate that DosS exists in the met form and that ferrous DosS is rapidly oxidized by $O_2$ to generate met DosS.

DosT is in the Oxy ($O_2$-Bound) Form.

Figure 5:
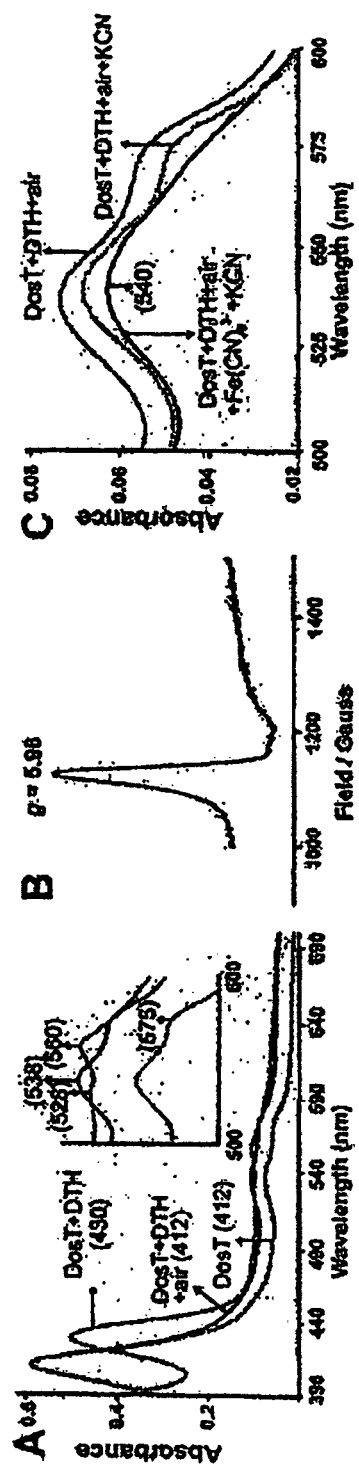
FIGS. 5 (A-C) show EPR and UV-visible spectroscopy characterization of DosT.

Having established that DosS is in the met form, whether exposure of DosT to oxygen converts its heme-iron to the met or the $O_2$-bound (oxy) form was examined. The absorption spectra of aerobically purified DosT was recorded and compared it with DTH exposed DosT. DTH exposure of DosT caused a red shift in Soret bands (412 to 430 nm), whereas the α and β bands produced a major and minor peak at 560 and 528 nm, respectively (FIG. 5A). When DTH treated DosT was re-exposed to air, the absorption spectrum rapidly reverted back to that of aerobically purified DosT (FIG. 5A). This behavior is consistent with the deoxy form reported for EcDOS (Delgado-Nixon et al., Biochemistry, 39:2685-91, 2000). In order to accurately determine the redox state of the heme-iron, EPR spectroscopy was utilized to demonstrate that air-exposed DosT generated no signal, showing the absence of a paramagnetic iron species. However, treatment of air-exposed DosT with the $Fe(CN)_6^{3-}$ generated a sharp signal at g=5.98 demonstrating that oxidized DosT contains a paramagnetic $Fe^{3+}$ species (FIG. 5B). The latter finding shows that air exposed DosT is in the oxygen bound (oxy) form similar to that of NifL, HemAT and EcDOS. Exposing DosT to air for 4 days at room temperature did not change the spectral properties and may indicate it is an unusually stable $O_2$-bound heme iron protein. To further confirm that DosT is in the oxy form, DosT was constantly stirred in a sealed cuvette for 2 hours under a constant flow of argon gas to allow replacement of bound oxygen, and the absorption spectra recorded. The spectra was virtually identical to the DTH exposed DosT spectra, showing that DTH or deoxygenation by argon gas converts oxy DosT ($Fe^{2+}$—$O_2$) into deoxy DosT ($Fe^{2+}$). To further corroborate that DosT is in the oxy form, air exposed DosT (up to 48 hours at room temperature) was treated with an excess of KCN, but no change in the absorption spectra was observed, demonstrating that DosT contains ferrous iron and is not capable of forming a complex with CN. However, when air exposed DosT was first treated with an excess of $Fe(CN)_6^{3+}$ followed by KCN, a peak at 540 nm was generated. This indicated that DosT contains $Fe^{2+}$ that can be oxidized by $Fe(CN)_6^{3+}$ to generate a $Fe^{3+}$ species, which can then react with KCN (FIG. 5C) to form a met CN complex. This spectroscopy data conclusively demonstrated that native air exposed DosT is in the stable, oxy form.

Example 2

NO and CO are Ligands of DosS and DosT

Despite the fact that DosS and DosT are known sensor kinases, no ligand for either protein has been identified. On the other hand, heme-based sensors are known to bind diatomic gases such as NO and CO (Gilles-Gonzalez, M. A. & Gonzalez, G. J. Inorg. Biochem., 99: 1-22, 2005) and, while NO has been shown to be essential for the control of acute and chronic infection of Mtb (Nathan, C. & Shiloh, Proc. Natl. Acad. Sci. USA, 97:8841-8, 2000; MacMicicing, J. D. et al., Proc. Natl. Acad. Sci. USA, 94:5243-8, 1997), there is no evidence to implicate CO in the active growth of Mtb.

In order to determine whether NO and CO are ligands of DosS or DosT, absorption and EPR spectroscopy was used to compare the spectral properties of DosS and DosT independently exposed to NO or CO. Since heme nitrosylation and carbonylation requires binding of NO or CO to deoxy ferrous heme-iron, DosS and DosT were first treated with DTH and then exposed to either the NO generator proline NONOate, or alternatively, to CO.

Figure 6:
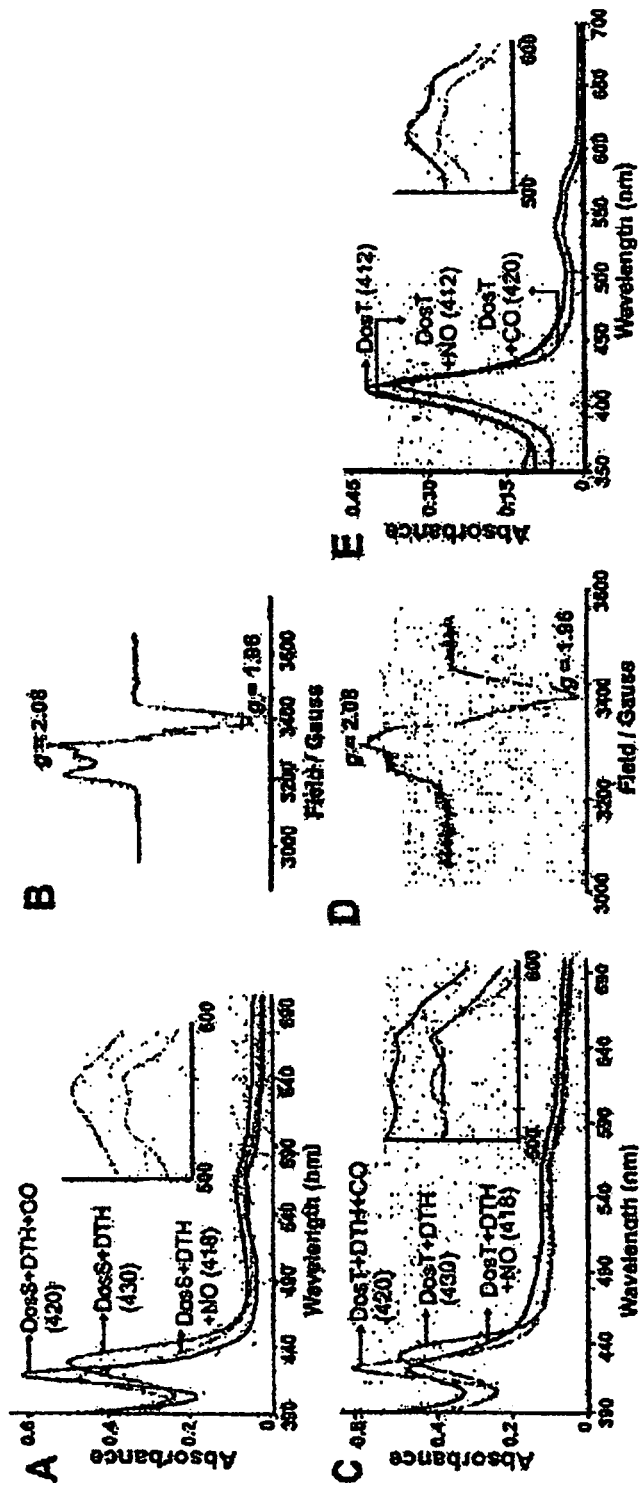
FIGS. 6 (A-E) show EPR and UV-visible spectroscopy results indicating that nitric oxide (NO) and carbon monoxide (CO) are ligands of DosS or DosT.

The absorption spectroscopy results shows that ferrous DosS treated with NO and CO generated heme-nitrosyl and heme-carbonyl DosS species as indicated by the changes in spectral properties (e.g, the shift in the Soret and appearance of distinct a and β bands) compared to unexposed ferrous DosS (FIG. 6A). These changes are highly characteristic of heme-NO and heme-CO complexes (Martin, E. et al., *J. Biol. Chem.*, 281:27836-45, 2006; Romberg, R. W. & Kassner, R. J., *Biochemistry*, 18:5387-92, 1979). To further validate that NO binds the heme iron of DosS, EPR spectroscopy was used. DosS was treated with DTH to generate ferrous DosS, and then exposed to proline NONOate. A highly characteristic nitrosyl-heme EPR spectrum (g=2.08) was obtained, demonstrating that NO binds DosS (FIG. 6B). Air exposed DosS was also treated with proline NONOate, but no EPR signal characteristic of a nitrosyl-heme species was generated. These experiments confirmed that only ferrous-DosS binds NO, which leads to the formation of a characteristic nitrosyl-heme complex (FIG. 6B).

In order to demonstrate that NO and CO are ligands of DosT, deoxy DosT was independently exposed to NO or CO. The spectral changes observed were highly characteristic of the formation of nitrosylated and carbonylated heme species (FIG. 6C). To further confirm that NO is a ligand of DosT, EPR was used to analyze deoxy DosT exposed to proline NONOate. Highly characteristic nitrosyl-heme EPR spectra were obtained, demonstrating that NO binds deoxy DosT (FIG. 6D). In addition, oxy DosT exposed to proline NONOate did not generate any detectable nitrosyl-heme species. These data indicate that NO is a ligand of DosT.

As an initial step towards examining whether NO and CO can generate heme-nitrosyl or heme-carbonyl complexes in the presence of $O_2$, oxy DosT was independently treated with CO or NO. Intriguingly, CO exposed, but not NO exposed oxy DosT caused a characteristic change in electronic absorption spectra (FIG. 6E), which is highly indicative of a heme-carbonyl complex. These results show that CO, but not NO can effectively substitute $O_2$ from oxy DosT. These data demonstrate that NO and CO are ligands of ferrous DosS and deoxy DosT. The data also shows that the binding of NO or CO is influenced by the redox state of DosS heme-iron and the oxidation state of DosT.

Example 3

DosS is a Redox Sensor

As $O_2$, NO, and CO are ligands for DosS and DosT, whether these ligands were regulatory ligands capable of affecting autophosphorylation of the histidine kinases was examined.

A met DosS sample was divided into two aliquots inside an anaerobic glove box. One aliquot was reduced with DTH whereas the other sample was left untreated. Both aliquots were then examined in the autokinase assay. The results showed that ferrous DosS possessed much higher autokinase activity than did met DosS (FIG. 7A) and show that ferrous DosS is in the "on" or active state. To verify this result, met DosS was deoxygenated, transferred to the glove box and reduced with DTH, which was subsequently removed via size-exclusion chromatography. The sample was divided into two aliquots; one aliquot was analyzed for autokinase activity inside the glove box, whereas the other sample was exposed to atmospheric air for 2 minutes prior to performing the autokinase activity. The results were essentially identical to those shown in FIG. 7A, further validating that ferrous DosS showed increased autokinase activity compared to met DosS.

Figure 7:
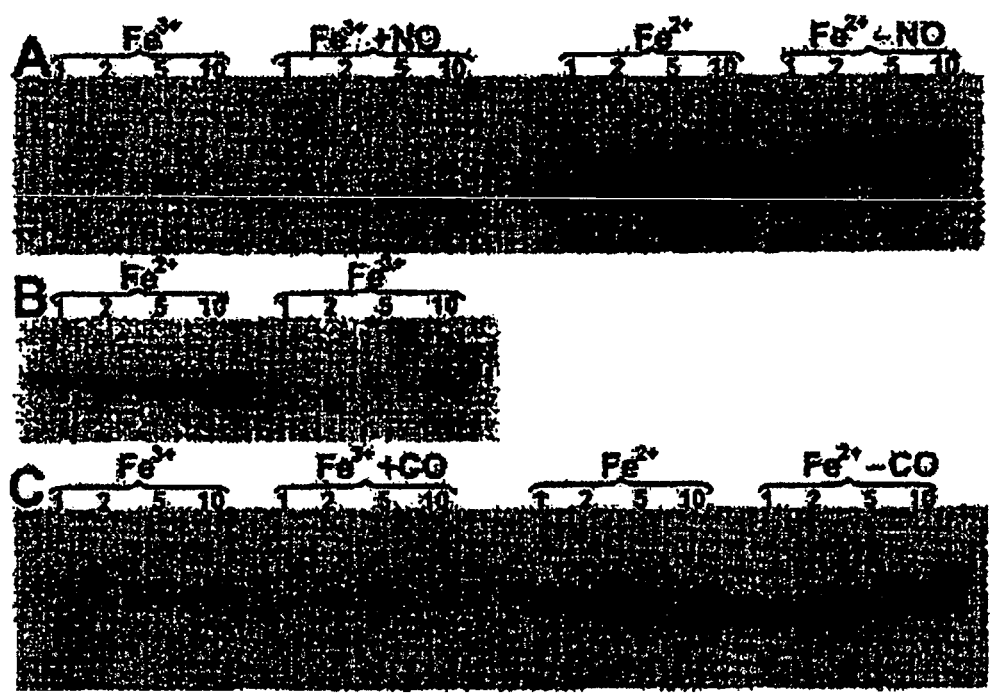
FIGS. 7 (A-C) show DosS activity in response oxygen ($O_2$), NO, and CO.

As an additional validation that the redox state of DosS heme-iron modulates autokinase activity $Fe(CN)_6^{3-}$ (rather than $O_2$) was used to oxidize DTH-reduced DosS and its effect on autokinase activity was analyzed. Similar to met DosS autokinase activity, the oxidation of ferrous DosS heme-iron by $Fe(CN)_6^{3+}$ to the ferric form also was found to inhibit DosS kinase activity (FIG. 7B). These data show that ferric DosS is in the "off" or inactive state.

Next, whether NO influenced DosS autokinase activity was assessed. This is an important experiment, largely because of the role of NO in protection against Mtb infection and because NO induces expression of the Dos regulon (Ohno, H. et al., *Cell Microbiol.*, 5:637-48, 2003). DosS was anaerobically reduced with DTH, exposed to proline NONOate and used in the autokinase reactions. Notably, relative to the inactive met form, nitrosylation of DosS significantly increased autokinase activity to levels comparable to active ferrous DosS autokinase activity (FIG. 7A). These results also show that NO is directly sensed by ferrous DosS through the formation of nitrosyl-heme complex. These data demonstrate that NO is a regulatory ligand of DosS and this result is consistent with the role of DosS in regulation of the Mtb Dos regulon.

CO was exploited as a chemical tool to probe the bioactivity of DosS and examine whether CO had any effect on DosS autokinase activity. Exposure of met DosS to CO was found not to generate any further autokinase activity. However, reduction of DosS with DTH followed by CO exposure producing CO-DosS resulted in significantly increased autokinase activity as compared to inactive met DosS (FIG. 7C).

These data demonstrate that molecular $O_2$ rapidly oxidizes ferrous DosS to met DosS, which dramatically decreases its autokinase activity. Thus, DosS is a redox sensor. In contrast, NO (and CO) binds ferrous DosS, which significantly enhances autokinase activity compared to inactive met DosS. Nonetheless, ligand binding is not required for DosS activity Rather, ligands (e.g., NO) may function to keep DosS in the "locked" (active) state. In addition, the biochemistry of DosS shows that DosS can directly modulate the expression of the Mtb Dos regulon in response to hypoxia and NO.

Example 4

DosT is a Hypoxia Sensor

Having established that NO, and CO are modulatory ligands of DosS, the effect of these ligands on DosT autokinase activity was also determined. An oxy DosT sample was transferred to the glove box and divided into two aliquots. One aliquot was treated with DTH to remove dissolved $O_2$ as well as the $O_2$ bound to DosT (deoxy) whereas the other samples were left untreated (oxy). The results demonstrated that deoxy DosT had significantly increased autokinase activity as compared to inactive oxy DosT (FIG. 8A), showing that the $O_2$ bound to DosT inhibits autokinase activity. As an additional verification, DosT was treated with DTH inside the glove box, followed by size-exclusion chromatography to remove the DTH. The sample was divided into two aliquots, and one aliquot was removed from the glove box and exposed to atmospheric air. The two samples were analyzed for autokinase activity inside the glove box (deoxy) and on the bench (oxy). The results were essentially identical to the experiment described above demonstrating that bound $O_2$ inhibits DosT autokinase activity.

Figure 8:
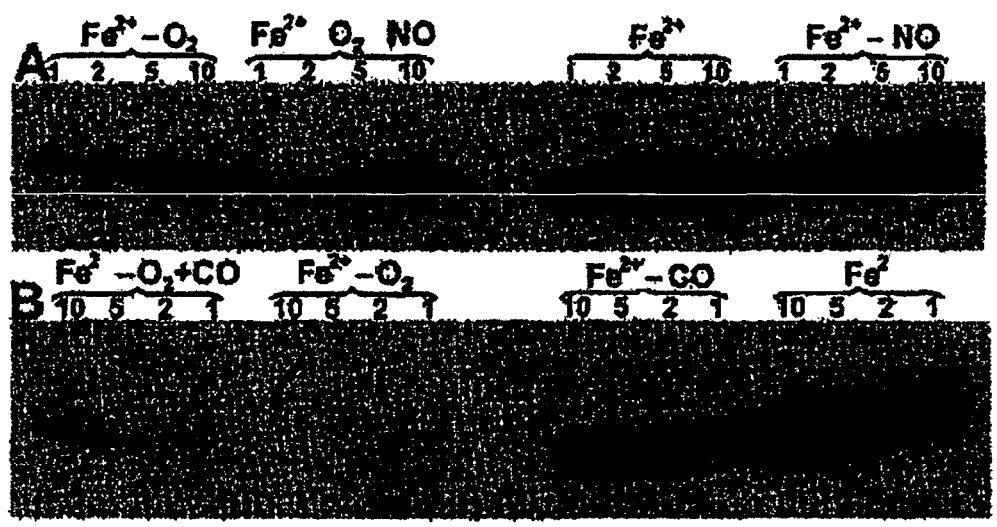
FIGS. 8 (A-B) show DosT activity in response to $O_2$, NO, and CO.

Next, the effect of NO on oxy and deoxy DosT was assessed. The samples were independently exposed to proline NONOate and analyzed for autokinase activity. NODosT showed significantly increased autokinase activity as compared to inactive oxy DosT. In fact, NO-DosT autokinase activity was found to be comparable to that of deoxy DosT (FIG. 8A). Importantly, as is the case for NO-DosS, these data are consistent with a role for NO-DosT in modulating expression of the Mfb Dos regulon.

Since the spectroscopic data (FIG. 6E) showed that CO can bind DosT in the presence of $O_2$, whether CO had any effect on oxy DosT autokinase activity was analyzed. Oxy DosT was divided (on the bench) into two aliquots, one was exposed to CO and the other was left untreated. Oxy DosT treated with CO showed significantly enhanced autokinase activity compared to inactive oxy DosT (FIG. 8B), further supporting our spectroscopy data that CO can replace bound $O_2$ to generate a heme-CO complex. Next, an oxy DosT sample was deoxygenated with argon gas and transferred to the glove box where it was reduced with DTH. The sample was divided into two aliquots, one was treated with CO and the other was left untreated; both were analyzed for autokinase activity. The data demonstrated that deoxy DosT showed the highest autokinase activity, followed by CO-DosT and finally oxy DosT.

Taken together, the spectroscopic and autokinase results demonstrate that $O_2$ bound to DosT inhibits autokinase activity whereas bound NO or CO enhance autokinase activity. Thus, DosT is an $O_2$-sensor. In addition, the results shows that DosT can directly modulate the expression of the Mfb Dos regulon in response to either hypoxia or NO, by altering its heme ligation state.

Taken together the results of Examples 1 through 4 indicate that $O_2$, NO, and CO are modulatory ligands of the sensor kinases DosT and DosS, which upon binding, alter the proteins' autokinase activity. Further, these results indicate that DosT and DosS are heme sensor kinases. Prior to these experiments, the ligand(s) and biochemical mechanism of DosS and DosT signal sensing and relay were unknown. As shown above, Mtb DosS functions as a redox sensor and DosT functions as a hypoxia sensor. Altogether, the model taught herein favors an ordered and coordinated, but complex response to enter and/or maintain a latent state. For example, DosS first has to be reduced before it can bind NO. Also, DosT first has to be deoxygenated to bind NO. Finally, ligands such as NO and $O_2$ can also operate alone, or in conjunction with each other.

Any patents or publications mentioned in the specification are indicative of the level of those skilled in the art to which the invention pertains These patents and publications are herein incorporated by reference in their entirety to the same extent as if each individual publication was specifically and individually indicated to be incorporated by reference.

The present invention is not limited in scope by the embodiments disclosed in the examples which are intended as illustrations of a few aspects of the invention and any embodiments which are functionally equivalent are within the scope of this invention. Various modifications of the methods and kits in addition to those shown and described herein will become apparent to those skilled in the art and are intended to fall within the scope of the appended claims. Further, while only certain representative combinations of the compositions or method steps disclosed herein are specifically discussed in the embodiments above, other combinations of the compositions or method steps will become apparent to those skilled in the art and also are intended to fall within the scope of the appended claims. Thus a combination of steps or compositions may be explicitly mentioned herein; however, other combinations of steps or compositions are included, even though not explicitly stated.

What is claimed is:

1. A method of screening for an agent that modulates the activation state of *Mycobacterium tuberculosis* (Mtb) comprising the steps of:
   (a) contacting one or more Mtb sensor kinases with the agent to be tested; and
   (b) detecting binding of oxygen, nitric oxide, carbon monoxide, or any combination thereof to one or more Mtb sensor kinases in the presence of the agent,
   a change in binding as compared to a control level of binding indicating the agent modulates the activation state of Mtb.

2. The method of claim 1, wherein binding is detected by detecting a change in a heme prosthetic group of the sensor kinase.

3. The method of claim 1, wherein the sensor kinase is DosS, DosT, or a combination thereof.

4. The method of claim 1, wherein the sensor kinase is DosS.

5. The method of claim 1, wherein the sensor kinase is DosT.

6. The method of claim 1, wherein a reduction in nitric oxide binding to the sensor kinase in the presence of the agent indicates the agent promotes reactivation of Mtb.

7. The method of claim 6, wherein the sensor kinase is deoxygenated prior to the contacting step.

8. The method of claim 1, wherein an increase in nitric oxide binding to the sensor kinase in the presence of the agent indicates the agent promotes latency of Mtb.

9. The method of claim 8, wherein the sensor kinase is deoxygenated prior to the contacting step.

10. The method of claim 1, wherein a reduction in oxygen binding or increase in carbon monoxide binding indicates the agent promotes latency of Mtb.

11. The method of claim 1, wherein an increase in oxygen binding or decrease in carbon monoxide binding indicates the agent promotes reactivation of Mtb.

12. A method of screening for an agent that modulates the activation state of *Mycobacterium tuberculosis* (Mtb) comprising the steps of:
   (a) contacting an Mtb sensor kinase with the agent to be tested; and
   (b) detecting a change in oxidation state of a heme iron in the Mtb sensor kinase,
   a change in oxidation state as compared to a control level oxidation state indicating the agent modulates the activation state of Mtb.

13. The method of claim 12, wherein the sensor kinase is DosS and the change in the oxidation state of the heme iron is an increase in the oxidation state.

14. The method of claim 12, wherein the sensor kinase is DosT and the change in the oxidation state of the heme iron is an increase in the oxidation state of a deoxygenated DosT.

15. The method of claim 12, wherein the Mtb sensor kinase is in the persistent state prior to the contacting step.

16. A method of screening for an agent that reactivates latent *Mycobacterium tuberculosis* (Mtb) comprising the steps of:
   (a) contacting one or more Mtb sensor kinases with nitric oxide or carbon monoxide;
   (b) contacting the Mtb sensor kinase with the agent to be tested; and
   (c) detecting the oxidation state and/or oxygenation state of a heme iron of the Mtb sensor kinase,
   an increase in oxidation or oxygenation as compared to a control indicating the agent reactivates Mtb.

17. A method of screening for an agent that prevents latency in *Mycobacterium tuberculosis* (Mtb) comprising the steps of:
(a) providing a Mtb sensor kinase DosS or DosT, wherein the DosS comprises a $Fe^{3+}$ heme iron and the DosT comprises a heme iron-oxygen complex;
(b) contacting the Mtb sensor kinase of step (a) with the agent to be tested;
(c) contacting the Mtb sensor kinase of step (a) with carbon monoxide or nitric oxide; and
(d) detecting the presence of $Fe^{3+}$ heme iron or heme iron-oxygen complex in the contacted Mtb sensor kinase, the presence of the $Fe^{3+}$ heme iron or heme iron-oxygen complex indicating that the agent prevents latency.

\* \* \* \* \*